United States Patent [19]

Gelb et al.

[11] Patent Number: 4,988,830
[45] Date of Patent: Jan. 29, 1991

[54] PROPYLENE OXIDE PRODUCTION

[75] Inventors: Morris Gelb, Bryn Mawr; David W. Leyshon; John A. Sofranko, both of West Chester; C. Andrew Jones, Newtown Square, all of Pa.

[73] Assignee: Arco Chemical Technology, Inc., Wilmington, Del.

[21] Appl. No.: 386,940

[22] Filed: Jul. 28, 1989

[51] Int. Cl.⁵ .................................. C07D 301/19
[52] U.S. Cl. ................................. 549/529; 585/640
[58] Field of Search .................... 549/529; 585/640

[56] References Cited

U.S. PATENT DOCUMENTS 3,351,635  11/1967  Kollar ................................ 549/529
4,849,573   7/1989  Kaeding ............................ 585/640

Primary Examiner—Richard L. Raymond
Assistant Examiner—Ba K. Trinh
Attorney, Agent, or Firm—William C. Long

[57] ABSTRACT

Present invention relates to the production of propylene oxide by reaction of propylene with a $C_4$ or higher hydroperoxide wherein at least a portion of the propylene is derived from the hydroperoxide moiety.

1 Claim, 1 Drawing Sheet

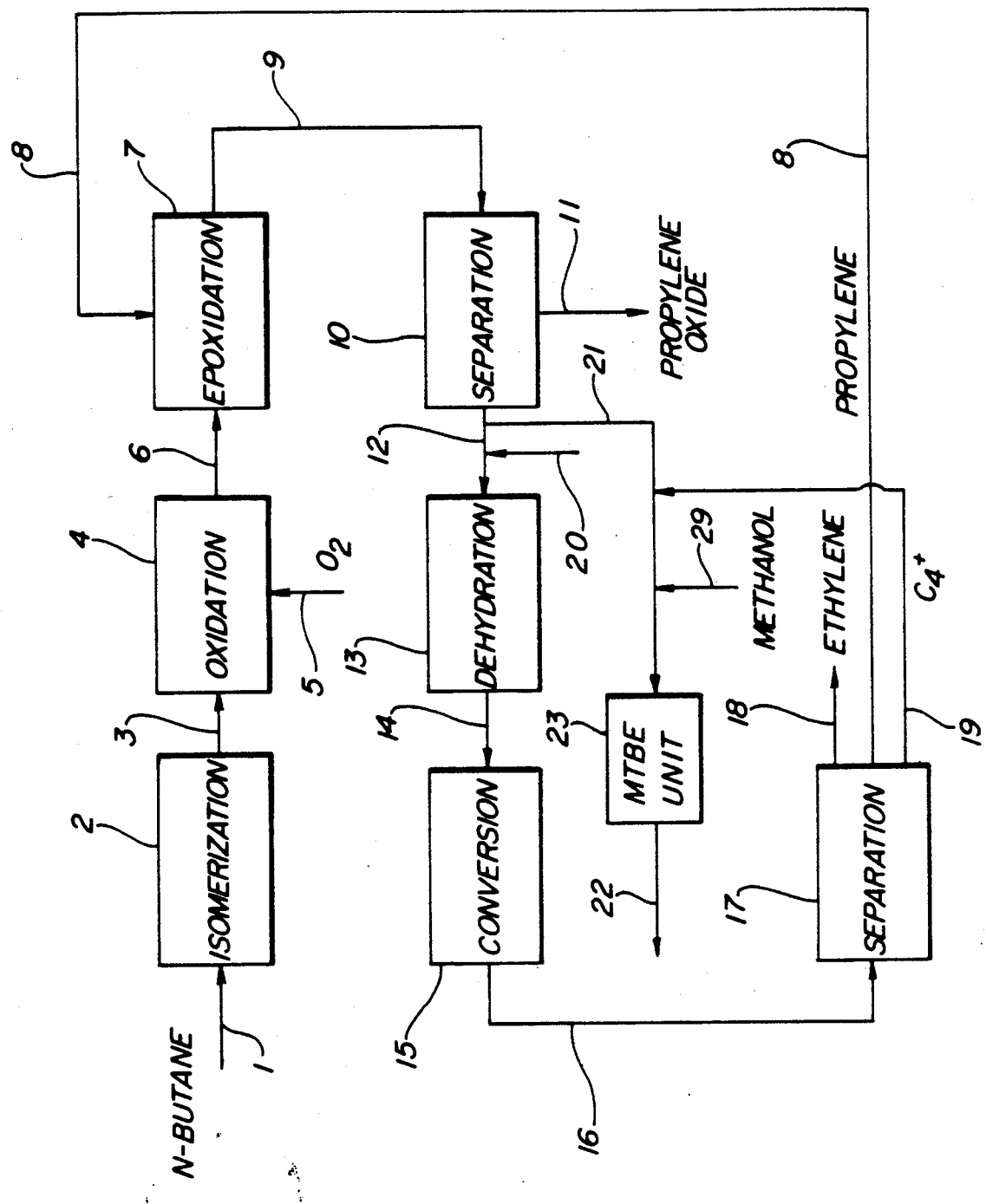

PROPYLENE OXIDE PRODUCTION

BACKGROUND OF THE INVENTION

1. Field of the Invention

The present invention relates to the production of propylene oxide by reaction of propylene with a $C_4$ or higher organic hydroperoxide, and especially to a process wherein at least a portion of the propylene used in the reaction is derived from the hydroperoxide.

2. Description of the Prior Art

The production of propylene oxide by the catalytic reaction of propylene with an organic hydroperoxide is a known and commercially practiced technology. See U.S. Pat. No. 3,351,635, for example. The hydroperoxide is converted to the corresponding alcohol during the said reaction and generally this product alcohol, itself, represents a useful co-product or it is converted to yet another more valuable co-product.

Commercially practiced processes include the reaction of propylene with t-butyl hydroperoxide (TBHP); the t-butyl alcohol (TBA) produced by this reaction is a valuable product in its own right, or it can be converted to methyl t-butyl ether (MTBE) which finds great value, specifically as a gasoline additive. Another commercial process involves the reaction of propylene with ethyl benzene hydroperoxide (EBHP) and conversion of the formed methyl benzyl alcohol (MBA) to styrene monomer.

In these commercially practiced technologies, the basic feedstocks are propylene and isobutane or ethylbenzene the latter materials being converted to the saleable products described above.

Problems arise, however, where there are substantial variations in the cost and availability of one feed material as compared to another, or where price and demand for one product varies substantially with respect to another product.

For example, in recent years, the cost per pound of propylene has risen sharply relative to $C_4$ hydrocarbons, while the availability of propylene has significantly declined. This has caused problems with the operations of the commercial units insofar as insuring adequate feed supplies.

SUMMARY OF THE INVENTION

In accordance with the invention, less costly and more readily available higher hydrocarbons comprise the basic feedstock for the ultimate propylene oxide product. The higher hydrocarbons are first oxidized to organic hydroperoxide. In the case of butanes or pentanes, this generally involves a first isomerization to isobutane or isopentane prior to oxidation. After oxidation, the resulting hydroperoxide reacted with propylene to form propylene oxide and the alcohol corresponding to the hydroperoxide, TBA in the case of TBHP, t-amyl alcohol (TAA) in the case of t-amyl hydroperoxide (TAHP), methyl benzyl alcohol (MBA) in the case of ethylbenzene, and the like. The alcohol from the epoxidation is converted to a propylene-containing reaction mixture, and this propylene is employed as feed propylene to the epoxidation step.

DESCRIPTION OF THE DRAWING

The attached drawing illustrates in schematic fashion practice of the invention.

DETAILED DESCRIPTION OF THE INVENTION

In a preferred practice of the invention, $C_4$ saturated hydrocarbons serve as the feedstock for some or all of the propylene oxide product. A commercial butane fraction is isomerized to form an isobutane-containing fraction and the isobutane is oxidized with molecular oxygen to form TBHP. This TBHP is reacted with propylene, obtained as later described, to form propylene oxide and TBA.

After separation of propylene oxide product, the TBA is converted to a propylene-containing mixture over a zeolitic catalyst. Where the zeolite is stable at elevated temperature in the presence of steam, the TBA can be fed directly to the reaction zone wherein it undergoes dehydration to isobutylene and the isobutylene is converted to a propylene-containing reaction mixture. Where the zeolite is unstable at elevated temperatures in the presence of steam, the TBA is first dehydrated to isobutylene and the isobutylene is separated and converted to a propylene-containing reaction mixture in a separate reaction step. In an especially advantageous practice of the invention, depending on their value at the time, various other compounds which are convertible to propylene in the zeolitic reaction zone can be added and converted with the isobutylene to the propylene-containing reaction mixture. Such added materials can comprise hydrocarbons including paraffins, olefins and mixtures, petroleum fractions such as an olefinic raffinate refining stream, and the like; oxygenates such as acetone, methanol, dimethyl ether, hexanoic acid and the like can also be used.

Conversion of the TBA or isobutylene is carried out over a zeolite catalyst under reaction conditions which promote conversion to propylene. Generally, as described in published European Patent Nos. 0 109059 and 0 109 060, such conditions involve high temperature and low hydrocarbon partial pressure.

In accordance with the subject invention, the propylene-containing reaction product mixture is separated into its various components. The ethylene product can comprise a product of the process or can be recycled to form additional propylene. Propylene is recovered and sent to the epoxidation reaction step where it is converted to propylene oxide product. Heavier materials can, in especially preferred practice, be converted to MTBE and/or used as gasoline blending agents, or these materials can be recycled for further conversion to propylene over the zeolitic catalyst.

From the above description, it can be seen that there is provided a process for propylene oxide production involving an integrated sequence of reaction steps and wherein the essential feed is a higher hydrocarbon such as butane. The inventive process has the important advantage of being independent of unpredictable variations in cost and availability of propylene as well as the market for TBA sales.

Reference is now made to the attached drawing for a further description of the inventive process. Referring to the drawing, the $C_4$ or higher hydrocarbon feed, preferably normal butane, comprises the basic feedstock to the process. This material is fed via line 1 to isomerization zone 2 wherein the normal butane is converted by known techniques to an isobutane-containing mixture. The reaction mixture from isomerization zone 2 is separated (not shown) and unreacted normal butane recycled to the isomerization. Isobutane formed in zone 2 passes via line 3 to oxidation zone 4 wherein it is contacted with molecular oxygen introduced through line 5 under conditions of elevated temperature whereby the isobutane is oxidized to tertiary butyl hydroperoxide. Appropriate conditions are described in U.S. Pat. No. 2,845,461, the disclosure of which is incorporated herein by reference. From zone 4 the hydroperoxide passes via line 6 to epoxidation zone 7 wherein the hydroperoxide is reacted with propylene which is introduced via line 8 and propylene oxide is produced. The conditions, catalysts and the like employed in the epoxidation are not themselves novel but are as illustrated, for example, in U.S. Pat. No. 3,351,635, the disclosure of which is incorporated herein by reference.

The epoxidation product mixture passes by means of line 9 to separation zone 10 wherein the product propylene oxide is recovered and removed via line 11. Other components of the reaction mixture, mainly comprising TBA, pass via line 12 to dehydration zone 13. As previously noted, where the zeolite catalyst which is employed in the production of the light olefins is sensitive to steam at elevated temperatures, the TBA should first be separately dehydrated, for example, over a stable dehydration catalyst such as alumina, in order to form isobutylene which is then reacted over the zeolite. Where the zeolite is stable in the presence of steam at elevated temperatures, the separate dehydration step can be omitted and the TBA fed directly to the zeolite reaction zone.

In the drawing, there is illustrated a first dehydration in zone 13 with the resulting isobutylene passing by means of line 14 to hydrocarbon conversion zone 15. In zone 15, the isobutylene is contacted with a zeolite catalyst such as ZSM-5 under conditions which favor the formation of lower olefins such as propylene. Appropriate conditions for this reaction generally involve low hydrocarbon partial pressures and high temperatures and space velocities.

As previously described, it is frequently advantageous to add via line 20 a supplemental stream of material which is converted to propylene in conversion zone 15. Such a supplemental stream is one which has, at the time, a relatively low value; examples include hydrocarbons preferably having 4 or more carbons including paraffins, olefins, raffinate streams comprised of both paraffins and olefins, and the like: oxygenates such as acetone, methanol, hexanoic acid and the like and mixtures thereof can be used.

By virtue of the addition of the above-mentioned supplemental propylene-forming feed via line 20, a portion of the TBA from epoxidation zone 7 can be removed via line 21 and converted, for example, to MTBE; in certain situations, this has distinct commercial advantages.

The reaction mixture exits from zone 15 by means of line 16 and passes to separation zone 17 wherein the component constituents are separately recovered. Ethylene is separated via line 18 and can comprise a product of the process. Product propylene is removed via line 8 and passes to epoxidation zone 7 as the essential propylene feedstock for propylene oxide production. Finally, heavier materials are separated by means of line 19. Although not shown, the ethylene and the $C_4^+$ heavier materials may be recycled to zone 15 for further conversion to propylene. In especially preferred practice, the heavy materials which contain a substantial amount of isobutylene pass via lines 19 and 21 to MTBE unit 23 for reaction with methanol introduced via line 24 to form MTBE. Product from unit 23 is recovered via line 22.

Conditions which are employed in reaction zone 15 involve elevated temperatures in the range of about 400° to 800° C., preferably 500° to 700° C. These temperatures are desirable to maximize propylene yields. Low hydrocarbon partial pressure is maintained.

Generally speaking, the basic feed material introduced via line 1 is hydrocarbon such as butane, pentane, cyclohexane, ethyl benzene and the like. In the case of nalkanes, these materials must first be converted by known isomerization procedures to derivatives such as tertiary carbon-containing materials suitable for oxidation to the hydroperoxide.

Alkane oxidation to the hydroperoxide is carried out in accordance with established procedures. See, for example, U.S. Pat. No. 2,845,461 which is referred to above.

As above described, the epoxidation is carried out as, for example, described in U.S. Pat. No. 3,351,635. Conventional separation procedures are employed.

For propylene production in conversion zone 15, the use of zeolites such as phosphorous treated ZSM-5 which are steam resistant is preferred. In this case, provision of separate dehydration zone 13 can be dispensed with.

In conversion zone 15, low hydrocarbon partial pressures favor propylene production. The feed can be admixed with steam or inert gas such as nitrogen. The hydrocarbon partial pressure is as low as practical, illustratively 1 to 30 psia. Where no diluents are employed, system pressures ranging from about −12 to 50 psig, preferably −5 to 30 psig are suitable. Higher pressures can be used when diluents are employed.

Space velocities depend on the particular zeolite used and are 1 to 5000 preferably 5 to 2000 $hr^{-1}$ WHSV. Reactor residence times are 0.001 to 20 seconds, preferably 0.01 to 5 seconds.

The conversion reaction of the instant invention in zone 15 may be exothermic or endothermic depending on the feed. For example, reaction with methanol is exothermic, but with TBA, the reaction is endothermic. For maximum flexibility, fluidized solid catalyst conversion procedures are preferred with the feed hydrocarbon vapor contacting fluidized particles of the zeolite catalyst. Heat of reaction is removed by removal of hot reaction products relative to the cold feed. A fixed bed adiabatic reaction is preferred for the case of an isobutylene feed, since the heat of reaction is minimal.

Zeolite catalysts used in the invention can be silaceous, crystalline molecular sieves. Such silica-containing crystalline materials include materials which contain, in addition to silica, significant amounts of alumina. These crystalline materials are frequently named "zeolites", i.e., crystalline aluminosilicates. Silica-containing crystalline materials also include essentially aluminum-free silicates. These crystalline materials are exemplified by crystalline silica polymorphs (e.g., silicalite, disclosed in U.S. Pat. No. 4,061,724 and organosilicates, disclosed in U.S. Pat. Re. No. 29948), chromia silicates (e.g., CZM), ferrosilicates and galliosilicates (see U.S. Pat. No. 4,238,318) and borosilicates (see U.S. Pat. Nos. 4,226,420; 4,269,813 and 4,327,236).

Crystalline aluminosilicate zeolites are best exemplified by ZSM-5 (see U.S. Pat. Nos. 3,702,886 and 3,770,614), ZSM-11 (see U.S. Pat. No. 3,709,979), ZSM-12 (see U.S. Pat. No. 3,832,449), ZSM-21 and ZSM-38

(see U.S. Pat. No. 3,948,758), ZSM-23 (see U.S. Pat. No. 4,076,842) and ZSM-35 (see U.S. Pat. No. 4,016,246).

Acid zeolites are especially preferred, particularly the ZSM type and borosilicates. ZSM-5 is especially useful. Phosphorous addition such as described in U.S. Pat. Nos. 4,044,065, 4,356,338 and 4,423,266 is very beneficial to selectivity to propylene, enhanced run length and high stability in the presence of steam.

In addition to the above, zeolite-containing materials can be used. Representative of such materials are zeolite A (U.S. Pat. No. No. 2,882,243), zeolite X (U.S. Pat. No. 2,882,244), zeolite Y (U.S. Pat. No. 3,130,007), zeolite ZK-5 (U.S. Pat. No. 3,247,195), zeolite ZK-4 (U.S. Pat. No. 3,314,752), synthetic mordenite and dealuminated mordenite, as well as naturally occurring zeolites, including chabazite, faujasite, mordenite and the like.

In general, the zeolites are ordinarily ion-exchanged with a desired cation to replace alkali metal present in the zeolite as found naturally or as synthetically prepared. The exchange treatment is such as to reduce the alkali metal content of the final catalyst to less than about 1.5 weight percent, and preferably less than about 0.5 weight percent. Preferred exchanging cations are hydrogen, ammonium, rare earth metals and mixtures thereof. Ion exchange is suitably accomplished by conventional contact of the zeolite with a suitable salt solution of the desired cation, such as, for example, the sulfate, chloride or nitrate salts.

It is preferred to have the crystalline zeolite in a suitable matrix, since that catalyst form is generally characterized by a high resistance to attrition, high activity and exceptional steam stability. Such catalysts are readily prepared by dispersing the crystalline zeolite in a suitable siliceous sol and gelling the sol by various means. The inorganic oxide which serves as the matrix in which the above crystalline zeolite is distributed includes silica gel or a cogel of silica and a suitable metal oxide. Representative cogels include silica-aluminia, silica-magnesia, silica-zirconia, silica-thoria, silica-beryllia, silica-titania, as well as ternary combinations, such as silica-alumina-magnesia, silica-aluminia-zirconia and silica-magnesia-zirconia. Preferred cogels include silica-aluminia, silica-zirconia, silica-alumina-zirconia and silica-magnesia-zirconia. The above gels and cogels will generally comprise a major proportion of silica and a minor proportion of the other aforementioned oxide or oxides. Thus, the silica content of the siliceous gel or cogel matrix will generally fall within the range of 55 to 100 weight percent, preferably 60 to 95 weight percent, and the other metal oxide or oxides content will generally be within the range of 0 to 45 weight percent, and preferably 5 to 40 weight percent. In addition to the above, the matrix may also comprise natural or synthetic clays, such as kaolin type clays, montmorillonite, bentonite or halloysite. These clays may be used either alone or in combination with silica or any of the above-specified cogels in a matrix formulation. The invention can be illustrated by the following example.

EXAMPLE

Referring to the drawing, about 215 lbs./hr. of a mixture of n-butane and isobutane is introduced via line 1 into isomerization zone 2. In zone 2, the n-butane is isomerized at 180° C. over a noble metal catalyst to form isobutane. Overall conversion of n-butane to isobutane is about 98%.

The reaction mixture from zone 2 is removed via line 3 with the unreacted n-butane being separated and recycled to zone 2 (not shown). Isobutane passes via line 3 into oxidation zone 4 wherein it is contacted with molecular oxygen introduced via line 5. In zone 4, the isobutane is converted to t-butylhydroperoxide (TBHP). Reaction conditions in zone 4 are a reaction temperature of 140° C., the overall isobutane conversion being 98% and the carbon selectivity to TBHP being about 52%. The TBHP product passes via line 6 to epoxidation zone 7 wherein it is reacted with propylene introduced via line 8 to form propylene oxide. Reaction conditions in epoxidation zone 7 are known, involving the use of a molybdenum catalyst, temperatures of 110° C. and a mole ratio of propylene to TBHP of 1.0.

The epoxidation reaction mixture passes from zone 7 via line 9 to separation zone 10. By conventional separation means, a product propylene oxide stream is removed and recovered via line 11.

Tertiary butyl alcohol (TBA) is formed from the TBHP during the epoxidation in zone 7 as well as during the oxidation of isobutane which occurs in zone 4. The TBA passes from separation zone 10 via line 12 to conversion zone 15 for conversion to lower olefins comprising ethylene and propylene. A portion of the TBA passes via line 21 to MTBE unit 23 wherein it is reacted to form MTBE after first being dehydrated (not shown). In this particular example, a phosphorous treated ZSM-5 catalyst is employed in zone 15 which catalyst is highly stable even in the presence of steam at high temperatures. Thus, in this example, there is no provision of the separate dehydration zone 13 which is illustrated in FIG. 1.

Supplementing the TBA feed to zone 15, there is added via line 20 about 20 lbs./hr. of acetone which is combined with 200 lbs./hr of the TBA, and together these materials are reacted in zone 15 over the phosphorous-containing ZSM-5 catalyst. Conditions in zone 15 include a temperature of 550° C. and a flow rate of 15 hr.$^{-1}$ WHSV. Yields which are achieved in zone 15 are shown on Table 1:

TABLE 1

| COMPONENT | YIELD, WT. % |
|---|---|
| Coke | 0.30 |
| $H_2$ | 0.02 |
| $CH_4$ | 0.07 |
| $C_2H_4$ | 5.02 |
| $C_2H_6$ | 0.05 |
| $C_3H_6$ | 35.25 |
| $C_3H_8$ | 1.71 |
| i-$C_4$ | 1.54 |
| BD | 0.12 |
| n-$C_4$ | 1.63 |
| butenes | 17.22 |
| $C_5^+$ | 11.57 |
| CO | 0.45 |
| $CO_2$ | 2.19 |
| $H_2O$ | 22.86 |

The reaction mixture from zone 15 passes via line 16 to a conventional separation zone 17. Ethylene is recovered as a product of the process by means of line 18. Propylene is recovered and passes via line 8 to epoxidation zone 7 where it is an essential reagent for the production of propylene oxide. Heavier materials including isobutylene are removed from zone 17 via line 19 and can either be further reacted to produce lower olefins or can be used as gasoline blending stock; in this example, these materials pass via lines 19 and 21 to MTBE unit 23, and the contained isobutylene is selectively reacted with methanol to form MTBE; methanol is fed via line 24. The MTBE unit operates in accordance with known procedures; temperature is about 90° C., and a ZSM-5 catalyst is used.

In this particular example, acetone is used to supplement the TBA feed to zone 15. This enables additional TBA from zone 7 to be converted to MTBE in zone 23.

The product mixture from MTBE unit 23 is removed via line 22. MTBE may be recovered. Higher hydrocarbons can be used as gasoline blending stock or may be recycled to zone 15 for further reaction to propylene.

The following table shows, in pounds, flows of material per hour at various points in the above example.

TABLE 2

| STREAM | FLOWS IN POUNDS PER HOUR | | | | | | | | | |
|---|---|---|---|---|---|---|---|---|---|---|
| | 1 | 3 | 5 | 6 | 8 | 9 | 11 | 16 | 20 | 21 | 22 |
| Coke | | | | | | | | 0.66 | | | |
| $H_2$ | | | | | | | | 0.05 | | | |
| $CH_4$ | | | | | | | | 0.16 | | | |
| $C_2H_4$ | | | | | | | | 11.03 | | | |
| $C_2H_6$ | | | | | | | | 0.11 | | | |
| $C_3H_6$ | | | | | 77.4 | | | 77.4 | | | |
| $C_3H_8$ | | | | | | | | 3.76 | | | 3.76 |
| $iC_4$ | 60 | 204 | | | | | | 3.39 | | | 3.39 |
| BD | | | | | | | | 0.26 | | | 0.26 |
| $nC_4$ | 155 | | | | | | | 3.54 | | | 3.54 |
| $iC_4^=$ | | | | | | | | 14.4 | | | |
| $nC_4^=$ | | | | | | | | 23.4 | | | 23.4 |
| $C_5^+$ | | | | | | | | 25.41 | | | 25.41 |
| Acetone | | | | | | | | | 20 | | |
| TBA | | | | 105 | | 240 | | | | 52 | |
| TBHP | | | | 165 | | | | | | | |
| PO | | | | | | 100 | 100 | | | | |
| MTBE | | | | | | | | | | | 82 |
| $O_2$ | | | 92.7 | | | | | | | | |
| Others | | | | 27 | | 35 | 20 | | | 3 | 3 |
| $H_2O$ | | | | | | | | 50.2 | | | |
| CO | | | | | | | | 0.98 | | | |
| $CO_2$ | | | | | | | | 4.80 | | | |
| TOTAL | 215 | 204 | 92.7 | 297 | 77.4 | 375 | 120 | 220 | 20 | 55 | 144 |

What is claimed is:

1. The process for the production of propylene oxide from saturated hydrocarbon having at least 4 carbon atoms which comprises:
    (a) oxidizing the said hydrocarbon to form a hydroperoxide having at least 4 carbon atoms;
    (b) reacting said hydroperoxide and propylene at epoxidation conditions to form propylene oxide and alcohol corresponding to the hydroperoxide;
    (c) separating the thus formed propylene oxide and alcohol;
    (d) converting at least a portion of the separated alcohol to propylene and hydrocarbons having at least 4 carbon atoms; and
    (e) feeding propylene formed in step (d) to the epoxidation of step (b).

2. The process for the production of propylene oxide from isobutane which comprises:
    (a) oxidizing the said isobutane to form t-butyl hydroperoxide;
    (b) reacting said t-butyl hydroperoxide and propylene at epoxidation conditions to form propylene oxide and t-butyl alcohol;
    (c) separating the thus formed propylene oxide and t-butyl alcohol;
    (d) converting at least a portion of the separated t-butyl alcohol to propylene and hydrocarbons having at least 4 carbon atoms; and
    (e) feeding propylene formed in step (d) to the epoxidation of step (b).

3. The process of claim 1 wherein the hydroperoxide is t-amyl hydroperoxide.

4. The process of claim 1 wherein the hydroperoxide is cyclohexyl hydroperoxide.

5. The process of claim 1 wherein the hydroperoxide is ethylbenzene hydroperoxide.

* * * * *